United States Patent [19]

Kurtz

[11] Patent Number: 4,685,908
[45] Date of Patent: Aug. 11, 1987

[54] DEVICE FOR DETECTING INCREASED PRESSURE IN PLEURAL CAVITY

[75] Inventor: Robert J. Kurtz, New York, N.Y.

[73] Assignee: BioResearch Ithaca Inc., Farmingdale, N.Y.

[21] Appl. No.: 813,512

[22] Filed: Dec. 26, 1985

Related U.S. Application Data

[63] Continuation-in-part of Ser. No. 662,498, Oct. 18, 1984, Pat. No. 4,617,020.

[51] Int. Cl.⁴ .............................................. A61M 1/00
[52] U.S. Cl. ..................................... 604/321; 73/747; 73/749; 73/705; 137/205
[58] Field of Search ................. 604/321; 73/747, 749, 73/705; 137/205

[56] References Cited

U.S. PATENT DOCUMENTS 1,955,315  4/1934  Styer ....................................... 73/705
4,544,370  10/1985 Elliott et al. ......................... 604/321

Primary Examiner—Leo P. Picard
Attorney, Agent, or Firm—Larson and Taylor

[57] ABSTRACT

A prebubble detector is provided for an underwater drainage apparatus. A series of sensors and detectors are disposed along the small arm of the underwater seal in a drainage device and means is provided for detecting the least degree of negativity reached during each breathing cycle. This information is fed to a logic circuit, timer and display so that the physician can readily see what the least degree of negativity reached is and how long a period of time has elapsed since the least degree of negativity has not decreased. A continuing trend of the least degree of negativity toward zero would indicate an air leak in the pleural cavity whereas stability of the least degree of negativity would indicate no air leak in the pleural cavity.

5 Claims, 5 Drawing Figures

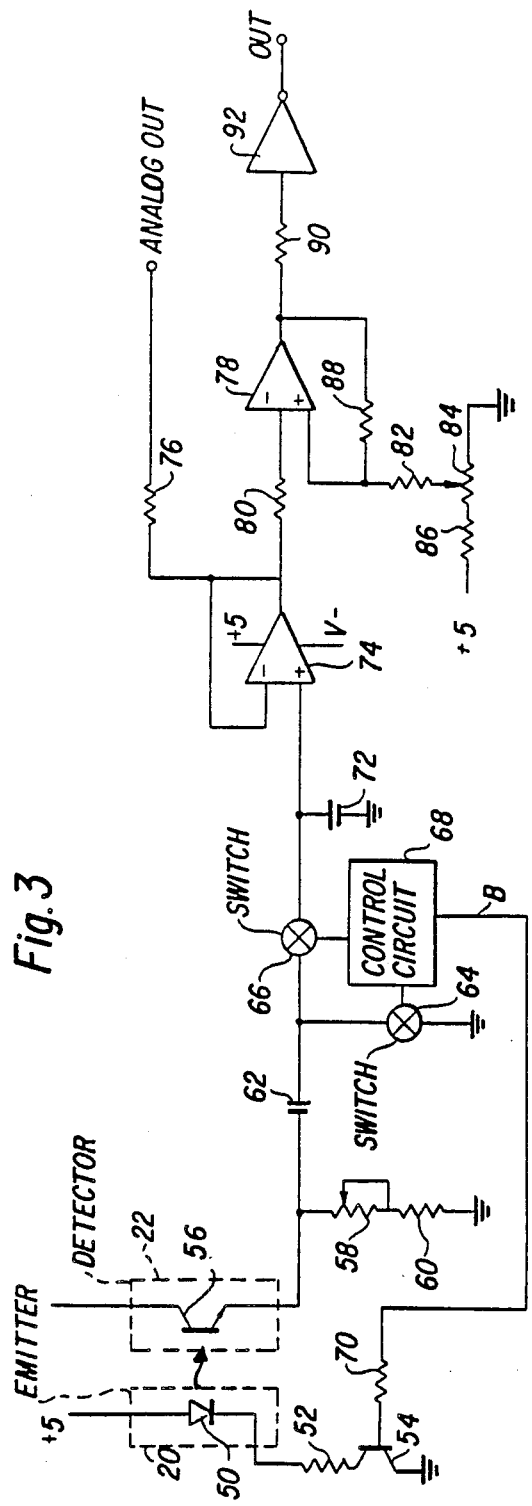
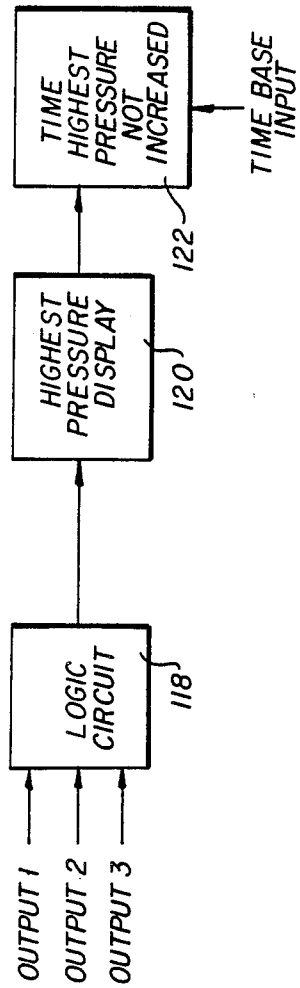

DEVICE FOR DETECTING INCREASED PRESSURE IN PLEURAL CAVITY

The present application is a continuation-in-part of application Ser. No. 662,498, filed Oct. 18, 1984 for "Air Leak Detector and Counter for Drainage Device" now U.S. Pat. No. 4,617,020.

BACKGROUND OF THE INVENTION

The present invention relates to a device for detecting increased pressure in pleural cavity which may be used with a drainage device and more specifically to a device for determining the highest pressure reached during the breathing cycle of a patient over a period of time and comparing the highest pressure reached with prior measurements over a time period.

There have been a number of prior art patents issued on pleural drainage devices utilizing underwater seals to insure that atmospheric air cannot enter the pleural cavity of the patient to which the device is connected. U.S. Pat. Nos. 3,363,626 and 3,363,627 are typical of prior art patent pleural drainage devices which include a collection chamber, underwater seal chamber and manometer chamber. A thoracotomy tube provides a passageway to innerconnect the collection chamber with the pleural cavity of a patient and a passageway is provided on the other side of the underwater seal to connect the drainage device to a source of suction. In operation the water level within the manometer chamber regulates the suction from the suction source to provide the desired degree of vacuum to the collection chamber and the pleural cavity of the patient. Fluids from the pleural cavity collect in the collection chamber and gases from the pleural cavity pass through the underwater seal in the form of bubbles.

Pleural drainage devices such as described above function well in maintaining the desired degree of vacuum in the pleural cavity and the underwater seal provides a means to prevent the entry of atmospheric air into the pleural cavity should, for example, the device become detached from the suction source. It has been found that the underwater seal also performs a further important function. Physicians examining the underwater seal can observe the passage of air bubbles through the seal and by monitoring the frequency of the passage of such bubbles can make a judgment as to the degree of air leak in the pleural cavity of the patient. This use of the underwater seal as a diagnostic tool is important and the present invention enhances this function so that the physician can more accurately determine the condition of the patient even though his time spent with the patient is relatively limited.

The difficulty encountered with prior art drainage devices such as referred to hereinbefore occurs when, for example, no bubbles pass through the underwater seal or only a single bubble passes through the seal during the period of time the physician is with the patient. Under these circumstances, the physician cannot determine the time interval between bubbles nor can he estimate the total volume of air passing out from the pleural cavity of the patient over a given period of time.

In prior application Ser. No. 662,498 referred to hereinbefore, there is disclosed an air leak detector and counter for a drainage device which provides a means for detecting the presence of a bubble passing through the underwater seal of a pleural drainage device and for transmitting a signal to a device which indicates the elapsed period of time between bubbles. Thus, the physician by observing a visual display provided by the device of the time elapsed since a bubble passed through the seal can immediately determine the condition of the patient and make a decision as to when the patient's pleural cavity is healed.

SUMMARY OF THE INVENTION

Normally, the pleural space is a closed sac within the space between the lungs and the rib cage and diaphragm. Normally, when there is no movement of the ribs or diaphragm, the interior of the lung, being directly connected to the atmosphere, is at atmospheric pressure. Also, the pleural space is normally at an approximate pressure of $-5$ cm $H_2O$. Because of the difference in pressure between the pleural space and the internal lung, the lung expands to the limits imposed by the rib cage, the diaphragm and the lung's own compliance. When the lung is normally compliant, the pleural space is obliterated with the visceral pleura of the lung in direct apposition with the parietal pleura of the rib cage and the diaphragm. During respiration, movement of the rib cage and diaphragm causes changes in the pleural space pressure resulting in expansion and contraction of the lung volume with a resultant exchange of gases as the patient goes through the cycle of inspiration and expiration.

In previous application Ser. No. 662,498 as discussed hereinbefore, there is provided means for detecting a bubble passing through the underwater seal of a pleural drainage device and for transmitting a signal to a device which indicates the elapsed time between bubbles or the quantity of bubbles per unit time which pass through the underwater seal. It must be realized that the passage of bubbles is basically a final event in the accumulation of increased pressure in the pleural space. In an underwater seal, the water level in the large arm and small arm are at the same height when the air pressure in the two arms is the same. When the large and small arm are filled to the 2 cm level and the pressure in the small arm of the water seal exceeds the pressure in the large arm of the water seal by 2 cm $H_2O$, bubbling will occur with air bubbles passing from the small arm through the water seal into the large arm. If the height of the fluid in the large arm is 3 cm above the level of water in the small arm of the Water seak U-tube manometer when bubbling into the large arm occurs, the differential pressure must be greater than 3 cm $H_2O$. Similarly, if the height of the water in the large arm is 0.5 cm higher than the level of water in the small arm when bubbling occurs, the differential pressure must have exceeded 0.5 cm $H_2O$. It is not, however, necessary to wait until bubbling from the small arm into the large arm is noted as provided in application Ser. No. 662,498 in order to determine that there will be no clinically significant leakage of air from the lung into the pleural space. It is possible to pass judgement on the clinical condition of the patient without waiting for bubbling to occur.

In normal respiration, there is an increase in negativity in the pleural space with inspiration by the patient. There is a decrease in negativity, i.e. the pleural space pressure becomes more positive, with expiration by the patient. By watching the maximum depression of the level of water in the small arm of the water seal, it can be determined when the air leaks into the pleural cavity, stops or slows sufficiently without ever having any bubbling from the small arm into the large arm of the water seal.

According to one embodiment of the present invention means is provided along the small arm of the water seal in a drainage device for detecting the lowest level reached by the fluid in the water seal which would correspond to the maximum pressure reached in the patient's pleural cavity during exhalation of air from the lungs. During normal breathing cycles the liquid within the small arm of the water seal will rise and fall between, for example, −3 centimeters of water to −12 centimeters of water. By measuring the maximum pressure, −3 centimeters of water, and by determining whether in repeated breathing cycles this maximum pressure does not further increase so as to approach zero and indicate the possible formation of a bubble, the condition of the patient's pleural cavity can be determined. The detecting means for determining the maximum pressure achieved during each breathing cycle is connected to a comparator which compares this number with previous breathing cycles and if the measurement shows a maximum pressure which is higher than any prior breathing cycles the comparator resets a timer. The timer thus provides a means for the physician to determine how long a period of time has elapsed since the maximum pressure reached in the pleural cavity has not changed.

An object of the present invention is to provide a detector for detecting increased pressure within the pleural cavity of a patient during a series of breathing cycles.

A further object of the present invention is to provide a device for determining the maximum pressure reached within the small arm of the underwater seal of a pleural drainage device during the breathing cycles of a patient.

Still another object of the present invention is to determine the maximum pressure reached in the small arm of an underwater seal of a drainage device and for measuring the length of time since the maximum pressure reached has not further increased.

Other objects and many of the attendant advantages of the present invention will become more readily apparent upon consideration of the following detailed specification in connection with the accompanying drawings.

BRIEF DESCRIPTION OF THE DRAWINGS

FIG. 3 is a schematic circuit diagram partly in block form, of a circuit constructed in accordance with a preferred embodiment of the invention;

FIG. 5 is a block diagram of an output and display unit constructed in accordance with a preferred embodiment of the invention.

DESCRIPTION OF THE PREFERRED EMBODIMENTS

Figure 1:
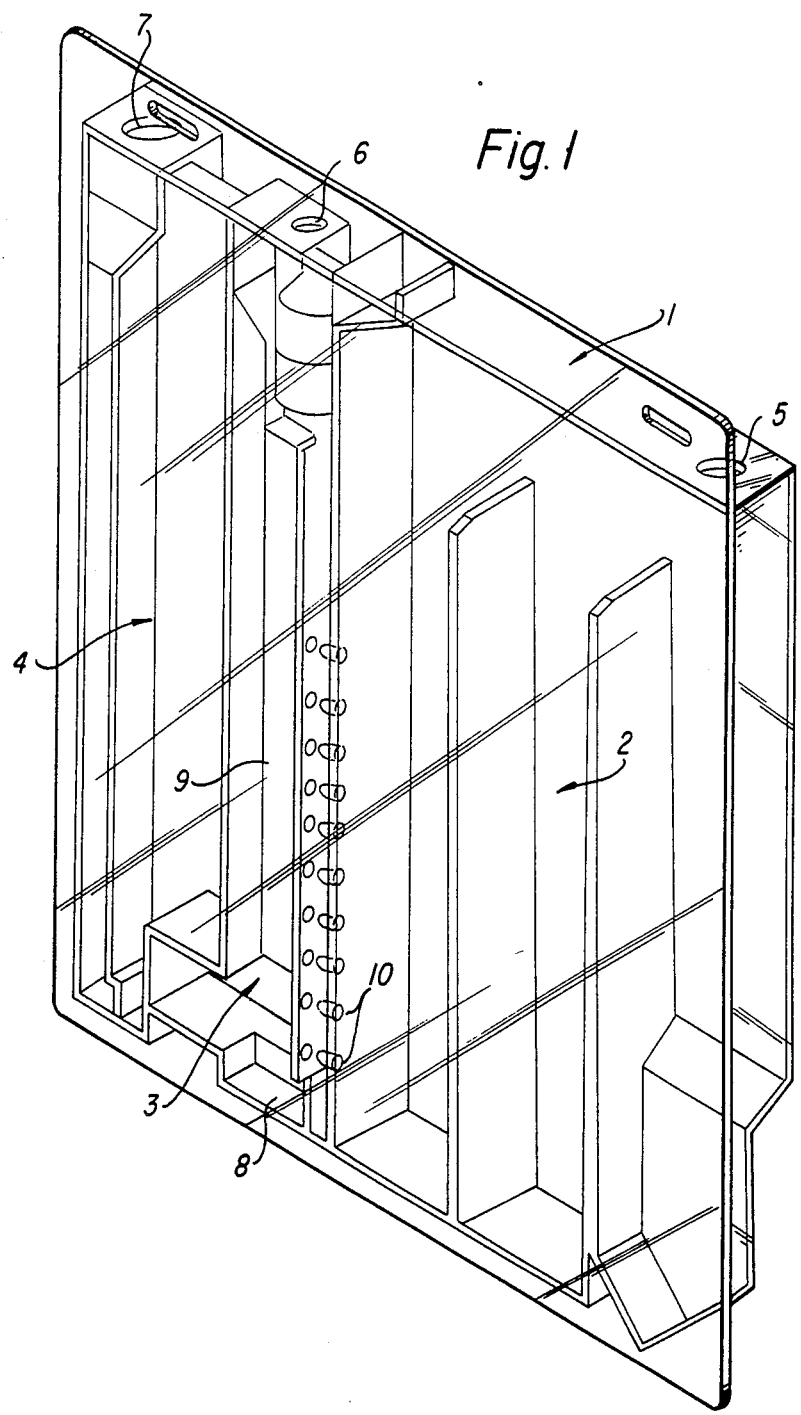
FIG. 1 is a perspective view of a drainage device with which the presently disclosed detector is used.

Referring now more specifically to the drawings wherein like nmumerals indicate like parts throughout the several views there is shown in FIG. 1 an underwater drainage device 1 including a collection chamber 2, an underwater seal chamber 3 and a manometer chamber 4. The drainage device has an inlet 5 which is connected by a thoracotomy tube with the pleural cavity of a patient. A connection 6 is provided for connecting the unit with a suction source and an outlet to atmosphere is provided at 7 for regulating the degree of suction applied to the collection chamber and the pleural cavity of the patient.

Figure 2:
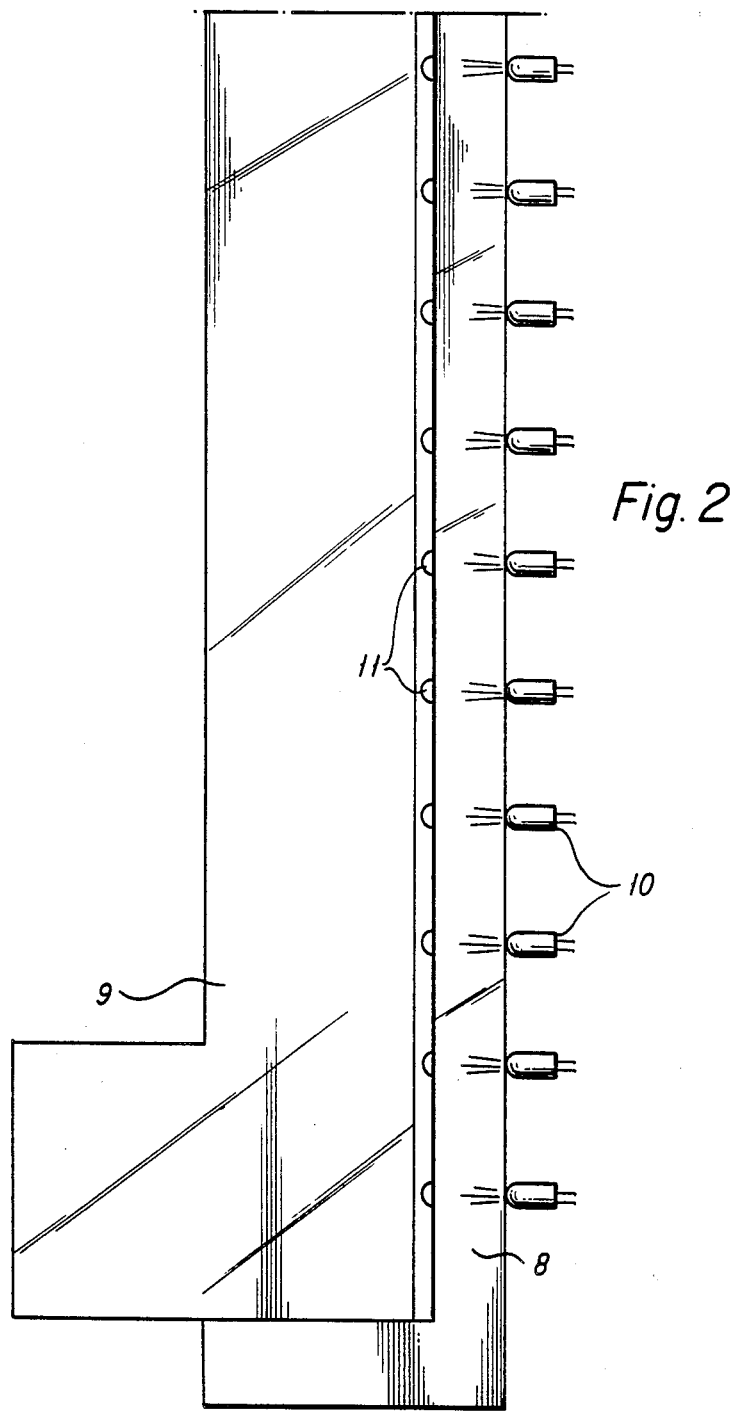
FIG. 2 is a vertical sectional view of FIG. 1 showing the underwater seal with the detector or sensors disposed adjacent thereto.

The underwater seal chamber has a small arm 8 and a large arm 9. The water within the small arm 8 of the underwater seal chamber will rise and fall with each inhalation and exhalation respectively during the breathing cycles of the patient. With no air leaks within the pleural cavity of the patient the maximum pressure reached during exhalation will remain approximately constant, for example, −3 centimeters of water. If, however, this level of maximum pressure increases, for example, to −1 or 0, it would indicate a possible air leak in the pleural cavity. The present invention provides a means for determining the maximum pressure reached during each breathing cycle of the patient by a series of sensors 10 disposed on one side of the small arm of the water seal with a series of detectors 11 disposed on the other side of the small arm of the water seal as shown in FIG. 2. The detectors disposed along the small arm of the water seal will detect the absence of water and will produce a signal indicative of the presence of air at each level at which air is present. Thus, the lowest level along the small arm of the water seal at which air is present will indicate the maximum pressure reached in the pleural cavity during each breathing cycle.

Figure 4:
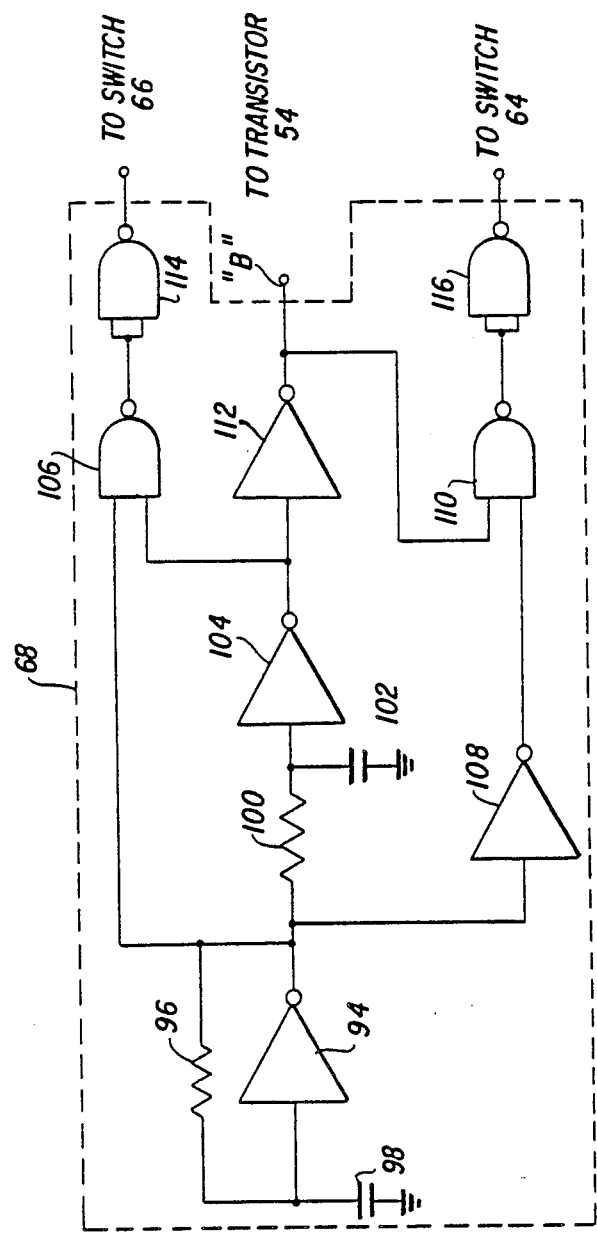
FIG. 4 is a schematic circuit diagram of the control circuit of FIG. 3.

Referring to FIG. 3, a schematic circuit diagram is shown of a preferred embodiment of the sensor circuit of the invention. A particular advantage of this circuit is that it provides immunity electronically from the effects of ambient light. Representative circuit values are indicated in the drawing. The light source or emitter 10 referred to above and denoted 20 in FIG. 3 is formed by a light emitting diode (LED) 50 which is connected in series with a control transistor 54 through a resistor 52. The light detector 11 referred to previously and denoted 22 in FIG. 3 is formed by a phototransistor 56 wherein receives light from LED 50. The emitter of phototransistor 56 is connected through the shunt combination of a variable resistor 58 and a fixed resistor 60, and a series capacitor 62, to a pair of switches 64 and 66 which are connected in shunt and series, respectively. Switching of switches 64 and 66 is controlled by a control circuit 68 which is shown in FIG. 4 and basically comprises an oscillator circuit used in driving LED 50 and phototransistor 56. As shown, one output of control circuit 68 is connected through a resistor 70 to the base of transistor 54. Switches 64 and 66, in combination with capacitor 62, a further shunt connected capacitor 72 and control circuit 68, basically operate as a sample and hold circuit for sampling and holding the output of the phototransistor 56. Control circuit 68 will be described in more detail below.

Switch 66 is connected through shunt capacitor 72 to one input of an operational amplifier 74 whch serves in buffering the input signal thereto. The output of operational amplifier 74 is connected through a resistor 76 to a "ANALOG OUT" output terminal as well as to one input of a further operational amplifier 78 through a series resistor 80. The other, plus input to operational amplifier 78 is connected through a resistor 82 to the tap of a potentiometer 84 connected in series with a fixed resistor 86. A feedback resistor 88 is connected between the output of operational amplifier 78 and the junction between resistor 82 and the plus input to operational amplifier 78. Operational amplifier 78 basically functions as a Schmitt trigger and serves to "square up" the input signal thereto. Potentiometer 84 is used to set the switching threshhold. The output of operational amplifier 78 is connected through a series resistor 90 to an inverter 92, which inverts and further buffers the signal and the output of which is the sensor output.

Referring to FIG. 4, the control circuit 68 includes an inverter 94 and shunt resistor 96 which form an oscillator circuit. A capacitor 98 is connected between the input to invester 94 and ground. The output of inverter 94 is connected through a phase shift network formed by a series resistor 100 and shunt capacitor 102 to a further inverter 104; to one input of a first NAND gate 106; and through a further inverter 108 to one input of a second NAND gate 110. The second input of the first NAND gate 106 is formed by the output of inverter 104, the latter also being connected to a further inverter 112. The output of inverter 112 is connected to the second input by the second NAND gate 110, and also forms the input "B" to transistor 54. In an exemplary embodiment, control circuit 68 provides switching of transistor 54 at a frequency of 1 KC.

The NAND gates 106 and 110 basically operate as differentiators, and their outputs are inverted by inverters 114 and 116 and form the inputs to series switch 66 and shunt switch 64, respectively. Considering this aspect of the operation of control circuit 68, the timing control provided thereby is such that just before LED 50 is turned on, switch 64 is turned on, thus grounding capacitor 62. The LED 50 is then turned on and the output of phototransistor 56 thur rises. Just before LED 50 is turned off, series switch 66 is turned on and the output of phototransistor 56 is transferred to capacitor 72 so that the voltage thereon is a measure of the change in detector voltage each cycle during when the light emitter, i.e., LED 50, is turned on and off.

A further purpose of control circuit 68 is to provide energy savings, particularly as used with battery powered units although it will be appreciated that this circuitry could be dispensed with and continuous operation of the sensor circuit provided for if desired.

Referring to FIG. 5, the system output circuitry is shown. Three sensor circuits corresponding to that shown in FIG. 3 are used, and these three circuits correspond to three sensor/detector combinations on the small arm of the underwater seal and the circuit outputs form the three inputs to a majority logic circuit 118. The presence of air between the sensor and detector causes an output to be produced. The output of logic circuit 118 is connected to a counter display unit 120 and to a reset input of a "time the maximum pressure has not increased" display unit 122. The former, i.e., unit 120, receives an input from all sensor/detector combinations and determines which signal represents the maximum pressure. Unit 122 receives a base input of very short duration (e.g., 0.1 seconds in an exemplary embodiment) and basically comprises a counter for counting the number of input pulses until reset by a new "maximum pressure" signal, so as to provide an indication of the time period the maximum pressure has not increased.

Although the invention has been described relative to exemplary embodiments thereof, it will be understood by those skilled in the art that variations and modifications can be effected in these exemplary embodiments without departing from the scope and spirit of the invention.

I claim:

1. A drainage device adapted to be connected to the pleural cavity of a patient comprising a collection chamber, a seal chamber in communication with said collection chamber, said seal chamber having a large arm and a small arm, and means disposed along the length of the small arm of the seal chamber for detecting the level of fluid in the small arm of the seal chamber, and means for recording the lowest level of fluid in the small arm of the seal chamber whereby the maximum pressure reached in the pleural cavity of a patient can be determined.

2. A drainage device according to claim 1 and further including means for determining the time elaspsed since the maximum pressure reached in the pleural cavity has not increased.

3. A drainage according to claim 1 wherein said detecting means includes a series of infrared light sources disposed along the length of the small arm of the seal chamber and sensor means for receiving infrared light from said light sources to determine when air is present between the light source and sensor and means for recording the lowest point on the length of the small arm of the seal chamber at which air is present.

4. A method of determining the pressure conditions in the pleural cavity of a patient comprising the steps of connecting the pleural cavity of a patient with a drainage device having a fluid seal chamber with a small arm and large arm therein, continuously determining the maximum pressure reached within the pleural cavity by measuring the lowest point reached on the small arm of the seal chamber and recording the lowest point measurement.

5. A method according to claim 4 and further including the steps of determining the time elapsed since the highest pressure reached within the pleural cavity has not increased.

* * * * *